United States Patent
Lee et al.

(10) Patent No.: US 9,820,997 B2
(45) Date of Patent: Nov. 21, 2017

(54) PHARMACEUTICAL COMPOSITION FOR TREATING DISEASE ASSOCIATED WITH DEMYELINATION OF NEURONS AND METHOD OF USING THE PHARMACEUTICAL COMPOSITION

(71) Applicant: Samsung Electronics Co., Ltd., Suwon-si, Gyeonggi-do (KR)

(72) Inventors: Yunil Lee, Yongin-si (KR); Kiyoung Chang, Yongin-si (KR); Sangchul Park, Seongnam-si (KR); Sungchun Cho, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/933,833

(22) Filed: Nov. 5, 2015

(65) Prior Publication Data

US 2016/0120884 A1    May 5, 2016

(30) Foreign Application Priority Data

Nov. 5, 2014   (KR) .................. 10-2014-0153180

(51) Int. Cl.
*A61K 31/635* (2006.01)
*A61K 31/145* (2006.01)
*A61K 31/167* (2006.01)
*A61K 31/63* (2006.01)

(52) U.S. Cl.
CPC .......... *A61K 31/635* (2013.01); *A61K 31/145* (2013.01); *A61K 31/167* (2013.01); *A61K 31/63* (2013.01)

(58) Field of Classification Search
CPC .................................................. A61K 31/635
See application file for complete search history.

(56) References Cited

U.S. PATENT DOCUMENTS

| | | |
|---|---|---|
| 7,576,101 B2 | 8/2009 | Karlik et al. |
| 2003/0191191 A1 | 10/2003 | Blume et al. |
| 2008/0293737 A1 | 11/2008 | Martinborough et al. |
| 2014/0221321 A1 | 8/2014 | Reeder et al. |
| 2016/0074380 A1* | 3/2016 | Hayden .............. A61K 31/4704 514/312 |
| 2016/0089340 A1 | 3/2016 | Cho et al. |
| 2016/0113890 A1 | 4/2016 | Koh et al. |

FOREIGN PATENT DOCUMENTS

| | | |
|---|---|---|
| KR | 10-2005-011412 A | 12/2005 |
| KR | 10-2005-0114212 A | 12/2005 |
| WO | WO 2013/152039 A1 | 10/2013 |
| WO | WO 2015/028659 A1 | 3/2015 |

OTHER PUBLICATIONS

Kim et al., "Promotion of Remyelination by Sulfasalazine in a Transgenic Zebrafish Model of Demyelination", *Molecules and Cells*, 38(11): 1013-1021 (2015).
Noseworthy et al., "The Mayo Clinic-Canadian cooperative trial of sulfasalazine in active multiple sclerosis", *Neurology*, 51:1342-1352 (1998).
European Patent Office, Extended European Search Report for Application No. 15193093.0, dated Mar. 4, 2016, 11 pages.
Chung, et al. "Generation of Demyelination Models by Targeted Ablation of Oligodendrocytes in the Zebrafish CNS," *Molecules and Cells*, 36 (1), 82-87, (2013).
Jung, et al. "Visualization of Myelination in GFP-Transgenic Zebrafish," *Developmental Dynamics*, 239, 592-597 (2010).

* cited by examiner

*Primary Examiner* — Yong Chong
(74) *Attorney, Agent, or Firm* — Leydig, Voit & Mayer, Ltd.

(57) ABSTRACT

A method of accelerating remyelination or suppressing demyelination of neurons in a mammal, and a method of treating a disease associated with demyelination of neurons in a mammal.

3 Claims, 16 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
ccaaattctt gctggtctgt g                    21

```
<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
catagatgac accgctgaga aggg                                          24
```

PHARMACEUTICAL COMPOSITION FOR TREATING DISEASE ASSOCIATED WITH DEMYELINATION OF NEURONS AND METHOD OF USING THE PHARMACEUTICAL COMPOSITION

RELATED APPLICATION

This application claims the benefit of Korean Patent Application No. 10-2014-0153180, filed on Nov. 5, 2014, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 698 Byte ASCII (Text) file named "721328_ST25.TXT," created on Oct. 15, 2015.

BACKGROUND

1. Field

The present invention relates to a pharmaceutical composition for treating a disease associated with demyelination, a method of accelerating remyelination of neuron cells in a mammal, including humans, by using the pharmaceutical composition, and a method of treating a disease associated with demyelination of neuron cells in a mammal.

2. Description of the Related Art

A demyelinating disease is a disease of the nervous system in which the myelin sheath of neurons is damaged. This damage impairs the conduction of signals in the affected nerves. In turn, the reduction in conduction causes deficiency in sensation, movement, cognition, or other functions depending on which nerves are affected. The demyelinating disease may include diseases affecting the central nervous system and peripheral nervous system. Demyelinating diseases of the peripheral nervous system include Guillain-Barre Syndrome and Charcot Marie Tooth (CMT) diseases. Demyelinating diseases of the central nervous system include multiple sclerosis. To date, ascorbic acid is a known effective treatment of peripheral neuropathy. However, there is a demand for alternative methods of treating these disorders.

SUMMARY

Provided is a pharmaceutical composition for treating a disease associated with demyelination of neurons in a mammal.

Also provided is a method of accelerating remyelination or suppressing demyelination of neurons in a mammal by administering a compound of Formula 1 or a pharmaceutically acceptable salt or solvate thereof to the mammal:

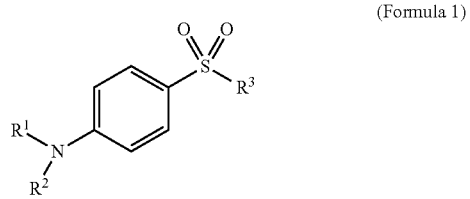

(Formula 1)

wherein, in Formula 1, $R^1$ and $R^2$ are each independently H or —(C=O)(C1-C6 alkyl), or $R^1$ and $R^2$ together are =N-phenyl, in which the phenyl is substituted with a carboxyl group and a hydroxyl group; and $R^3$ is an aminophenyl in which the amino group is optionally substituted with —(C=O)(C1-C6 alkyl); or —$NR^6R^7$, wherein —$R^6$ and $R^7$ are each independently H, —(C=O)(C1-C6 alkyl), or a heteroaryl having 3 to 8-membered ring atoms.

Further provided is a method of treating a disease associated with demyelination of neurons in a mammal by administering a compound of Formula 1 to the mammal.

These and/or other aspects will become apparent and more readily appreciated from the following description of the exemplary embodiments, taken in conjunction with the accompanying drawings.

DETAILED DESCRIPTION

Figure 1A:
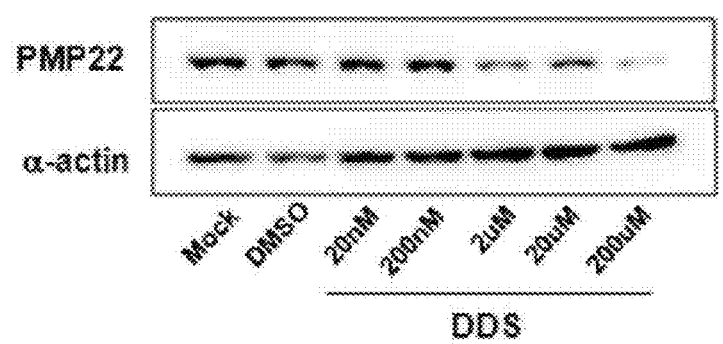
FIGS. 1A and 1B illustrate α-PMP22 gene expression of SH-SY5Y cells in the presence of DDS measured by Western blot.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

According to an aspect of an exemplary embodiment, a pharmaceutical composition for treating a disease associated with demyelination of neurons in a mammal includes a compound represented by Formula 1; or a pharmaceutically acceptable salt or solvate of the pharmaceutical composition.

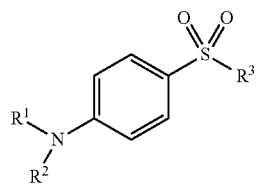

(Formula 1)

In Formula 1, $R^1$ and $R^2$ are each independently H or —(C=O)(C1-C6 alkyl), or $R^1$ and $R^2$ together constitute =N-phenyl, in which the phenyl is substituted with a carboxyl group and a hydroxyl group; and $R^3$ is an aminophenyl, in which an H of the amino group is optionally substituted with —(C=O)(C1-C6 alkyl), or $R^3$ is —$NR^6R^7$, in which —$R^6$ and $R^7$ are each independently H, —(C=O)(C1-C6 alkyl), or a heteroaryl having 3- to 8-membered cyclic atoms.

In an embodiment of Formula 1, $R^1$ and $R^2$ are each independently H or —(C=O)(C1-C6 alkyl); and $R^3$ is an aminophenyl, in which the amino group is optionally substituted with —(C=O)(C1-C6 alkyl). The C1-C6 alkyl may be linear, for example, a linear C1-C3 alkyl group. In another embodiment $R^1$ and $R^2$ are each independently H, and $R^3$ is 4-aminophenyl to provide dapsone (DDS). In another embodiment, $R^1$ and $R^2$ are each independently H, and $R^3$ is 4-acetylaminophenyl, providing mono N-acetyldapsone (MADDS).

In a further embodiment of Formula 1, $R^1$ and $R^2$ are each independently H, or $R^1$ and $R^2$ together constitute =N-phenyl, in which a hydrogen of the phenyl is substituted with a carboxyl group and a hydrogen of the phenyl is substituted with a hydroxyl group; and $R^3$ is an aminophenyl or —$NR^6R^7$, in which —$R^6$ and $R^7$ are each independently H, —(C=O)(C1-C6 alkyl), or a heteroaryl having 3- to 8-membered cyclic atoms. The heteroaryl having 3- to 8-membered cyclic atoms may be a pyridyl. In the compound, —(C=O)(C1-C6 alkyl) may be —(C=O)(linear C1-C3 alkyl). $R^1$ and $R^2$ may together constitute =N-phenyl, in which a hydrogen of the phenyl is substituted with a carboxyl group and a hydrogen of the phenyl is substituted with a hydroxyl group; and $R^3$ may be —$NR^6R^7$, in which $R^6$ is H, and $R^7$ is a 6-membered nitrogen-containing ring (e.g.,

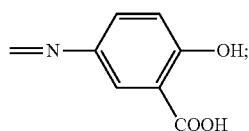

pyridine). For example, $R^1$ and $R^2$ may together constitute and $R^3$ may be a pyridinyl-NH—, in which $R^6$ may be H, and $R^7$ may be a pyridinyl. Or, $R^1$ and $R^2$ may together constitute

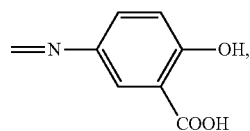

and $R^3$ may be

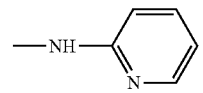

providing sulfasalazine (SSZ). In another embodiment, $R^1$ and $R^2$ are both H; and $R^3$ is —NH—(C=O)(C1-C6 alkyl). For example, $R^1$ and $R^2$ are both H; and $R^3$ is acetyl-NH—, providing sulfacetamide (SCM).

The compound may be in the form of a pharmaceutically acceptable salt of any of the foregoing compounds of formula 1. Examples of the salt may include acid addition salts that are commonly used in the field of pharmaceuticals including salts derived from inorganic acids such as hydrochloric acid, hydrobromic acid, sulfuric acid, sulfamic acid, phosphoric acid, or nitric acid; and salts derived from organic acids such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxy-benzoic acid, fumaric acid, toluenesulfonic acid, oxalic acid, or trifluoroacetic acid. Also, examples of the salt may include common metal salts, for example, salts derived from metals such as lithium, sodium, potassium, magnesium, or calcium. The acid addition salt or the metal salt may be prepared according to a common method in the art.

The compound may be in the form of a solvate of formula 1. The term "solvate" refers a complex that is constituted of at least one solute molecule, that is, a compound represented by Formula 1 or a pharmaceutically acceptable salt of the compound; and at least one solvent molecule. The solvate may be, for example, a complex formed with water, methanol, ethanol, isopropanol, or acetic acid.

The compound may be in the form of a stereoisomer of the compound. Examples of the stereoisomer include all types of stereoisomers such as enantiomers and diastereomers. The compound may be in the stereoisomerically pure form of a stereoisomer or a mixture of at least two stereoisomers, for example, a racemic mixture. Isolation of a specific stereoisomer may be performed by using one of the known methods in the art.

Regarding the compound, the composition, and the method of the inventive concept, the terms used herein have the meanings defined below unless stated otherwise.

The term "alkyl" denotes a linear or branched monovalent saturated hydrocarbon group. Unless defined otherwise, the alkyl group generally includes 1 to 6, 1 to 5, 1 to 4, or 1 to 3 carbon atoms. The alkyl group may include, for example, methyl, ethyl, propyl (e.g., n-propyl or iso-propyl), butyl (e.g., n-butyl, iso-butyl, or t-butyl), pentyl (e.g., n-pentyl, iso-pentyl, and neopentyl), and n-hexyl.

The term "aryl" denotes an aromatic hydrocarbon group having a monocyclic or a polycyclic ring. The polycyclic aromatic hydrocarbon group may include one having a fused ring (e.g., naphthalene) and/or a non-fused ring (e.g., biphenyl). The polycyclic aromatic hydrocarbon group may have two, three, or four rings. Unless defined otherwise, the aryl group may generally have 3 to 8, 4 to 7, 5 to 7, 5 to 6, or 6 carbon atoms on the ring. The aryl group may include, for example, a phenyl.

The term "heteroaryl" denotes a monovalent aromatic group having at least one heteroatom selected from the group consisting of N, O, and S as a ring-constituting member. The heteroaryl group may have a monocyclic or polycyclic structure. The polycyclic structure may have, for example, two, three, or four condensed rings. Unless defined otherwise, the heteroaryl group may generally include 3 to 8, 4 to 7, 5 to 7, 5 to 6, or 6 carbon atoms on the ring. The heteroaryl group may include one, two, or three heteroatoms. The heteroaryl group may include, for example, pyridyl, N-oxopyridyl, pyrimidinyl, pyrazinyl, pyridazinyl, triazinyl, furyl, thienyl, imidazolyl, furanyl, thiazolyl, oxazolyl, iso-oxazolyl, triazolyl, tetrazolyl, 1,2,4-thiadiazolyl, or isothiazolyl.

The compound of Formula 1 may be dapsone (4,4'-diaminodiphenylsulfone, DDS), N-acetyldapsone (NADDS), sulfasalazine (2-hydroxy-5-[(E)-2-{4-[pyridin-2-yl)sulfamoyl]phenyl}diazen-2-yl]benzoic acid SSZ), or sulfacetamide (N-[(4-aminophenyl)sulfonyl]acetamide, SCM). Dapsone is an antibacterial agent that is most commonly used in combination with rifampicin and clofazimine as a multidrug therapy (MDT) for the treatment of leprosy caused by *Mycobacterium leprae*. Dapsone is industrially usable as a topical and oral formula. A trade name of the topical dapsone is ACZONE™, and a 5% gel type of the topical dapsone is available from Allergan. Dapsone was first synthesized by Fromm and Wittmann in 1908. In order to synthesize dapsone by one exemplary method, 4,4'-dinitrodiphenyl sulfide is oxidized to sulfone in a solution including potassium dichromate, glacial acetic acid, and sulfuric acid. The nitro group is reduced by Sn and concentrated hydrochloric acid and treated with an alkaline to prepare a free base. NADDS is a metabolite of DDS, and at least one of two amino groups of DDS may be acetylated to synthesize NADDS. Hereinafter, an acetylated compound of one of the two amino groups of DDS is also referred to as MADDS.

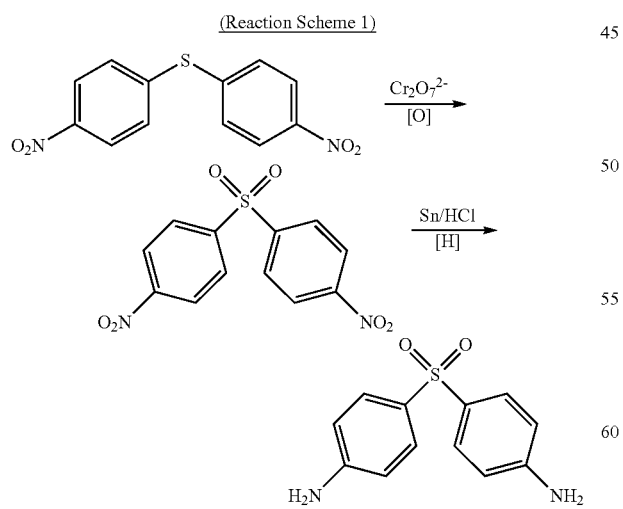

Sulfasalazine (brand name Azulfidine in the U.S., Salazopyrin and Sulazine in Europe and Hong Kong) was developed in the 1950s specifically to treat rheumatoid arthritis (RA). Sulfasalazine is a sulfa drug, a derivative of mesalazine, and is formed by combining sulfapyridine and salicylate with an azo bond. Sulfasalazine is used in the treatment of inflammatory bowel disease (IBD), including ulcerative colitis and Crohn's disease. Also, sulfasalazine is used in the treatment of RA and used in other types of inflammatory arthritis (e.g., psoriatic arthritis) where it has a beneficial effect. U.S. Pat. No. 2,396,145 discloses, for example, a synthesis method of the sulfasalazine. A pharmaceutically acceptable derivative of sulfasalazine may be synthesized by using a method known in the art.

Sulfacetamide is a sulfonamide antibiotic. A sulfacetamide 10% topical lotion, available in the trade names Klaron or Ovace, is approved for the treatment of acne and seborrheic dermatitis. Synthesis of sulfacetamide may be performed according to Reaction Scheme 2. In the last process of Reaction Scheme 2, an $N^4$-acetyl group is selectively removed by alkali hydrolysis.

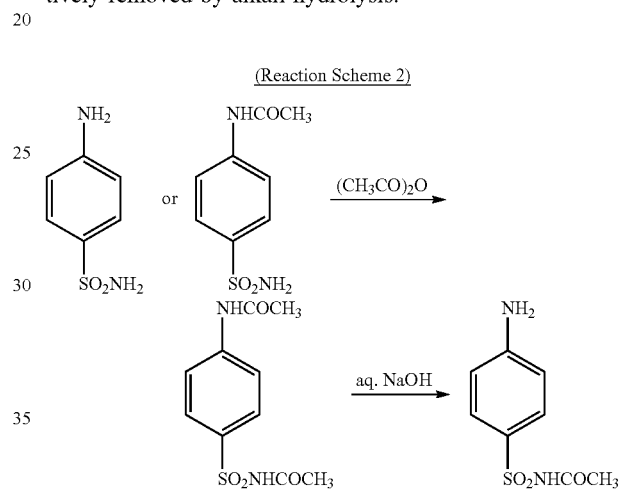

Also, the compound may be synthesized during a synthesis process of sulfonamide or its derivative. The compound may be, for example, synthesized according to Reaction Scheme 3. First, acetanilide (1), which is a starting material, is commercially available. The acetanilide (1) is reacted with chlorosulfonic acid while heating the reaction solution (e.g., at a temperature of about 70° to about 80°) to synthesize 4-acetamidobenzenesulfonyl chloride (2). The 4-acetamidobenzenesulfonyl chloride (2) is reacted with $R^6R^7NH$ while heating the reaction solution (e.g., at a temperature of about 70° to about 80°) to synthesize Compound 3. Next, $N^4$-acetyl group is hydrolyzed by incubating Compound 3 under an alkali condition to obtain Compound 4. Compound 4 is reacted with Compound 5 to be linked through azo coupling (in this case, $R^1$ and $R^2$ may together form

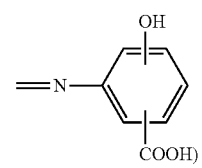

or to be acylated to synthesize Compound 6.

(Reaction Scheme 3)

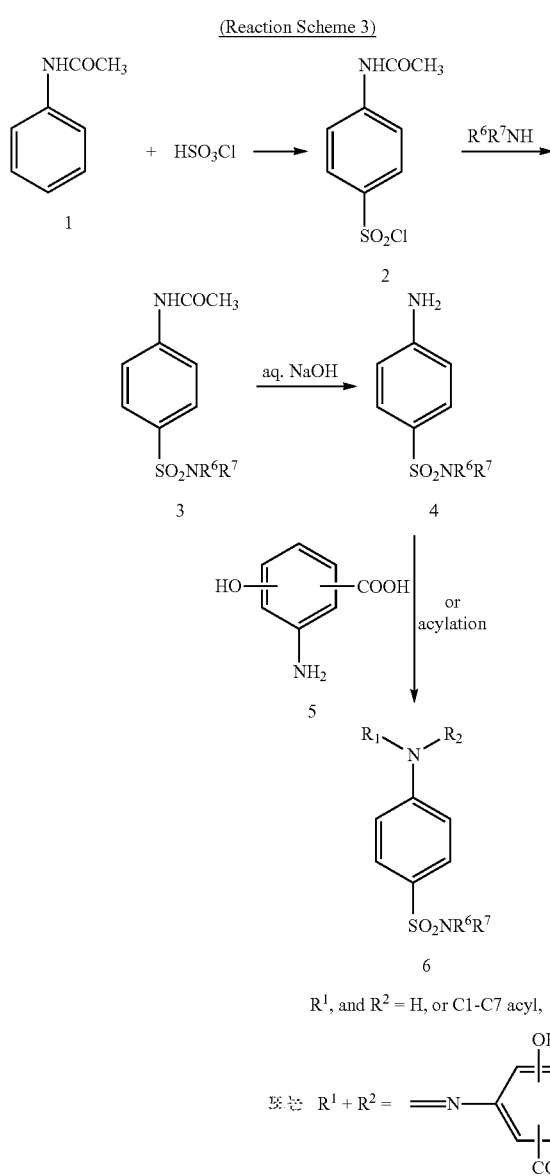

A disease associated with demyelination of neurons (also, referred to as "demyelinating disease") is a disease of the nervous system in which the myelin sheath of neurons is damaged. This damage impairs the conduction of signals in the affected nerves, which, in turn, causes deficiency in sensation, movement, cognition, or other functions depending on which nerves are involved. The disease may include diseases affecting the central nervous system (also, referred to as "central nervous system demyelinating diseases") and peripheral nervous system (also, referred to as "peripheral nervous system demyelinating diseases"). The central nervous system demyelinating diseases include multiple sclerosis, Devic's disease, inflammatory demyelinating diseases, central nervous system neuropathies like those produced by Vitamin B12 deficiency, myelopathies like Tabes dorsalis, leukoencephalopathies like progressive multifocal leukoencephalopathy, leukodystrophies, or a combination thereof. The peripheral nervous system demyelinating diseases include Guillain-Barre syndrome and its chronic counterpart, chronic inflammatory demyelinating polyneuropathy, anti-MAG peripheral neuropathy, Charcot Marie Tooth (CMT) disease, copper deficiency, progressive inflammatory neuropathy, or a combination thereof. The diseases may be multiple sclerosis, Guillain-Barre syndrome, CMT, or a combination thereof. The CMT may be a CMT1A sub-type, CMT1E sub-type, or CMT3 sub-type.

The diseases may be caused by overexpression of peripheral myelin protein 22 (PMP22). PMP22 is a protein which in humans is encoded by the PMP22 gene. The integral membrane protein encoded by this gene is a hydrophobic, tetraspan glycoprotein expressed mainly in Schwann cells and is a major component of compact myelin in the peripheral nervous system. PMP22 has been known to interact with myelin protein zero. Various mutations of the gene are causes of CMT1A, Dejerine-Scottas disease, and hereditary neuropathy with liability to pressure palsy (HNPP). CMT1A is the most common form of the disease, comprising at least 60% of all CMT patients. CMT1A is caused by a duplication of the PMP22 gene on Chromosome 17. Instead of having two copies of the gene, the chromosome may have three copies, two on one chromosome and one on the other chromosome.

The compound of Formula 1 or pharmaceutical composition comprising same may be administered to any mammal in need thereof. The mammal may be a human. The mammal may have demyelinated neurons and/or a disease associated with demyelination.

The composition may further include a pharmaceutically acceptable carrier. Regarding the composition, the term "pharmaceutically acceptable carrier" as used herein denotes a material that is used in combination with an active ingredient, that is, generally, an inert material, to help application of the active ingredient. Examples of the carrier may include, in general, a pharmaceutically acceptable excipient, additive, or diluent. Examples of the carrier may include at least one selected from the group consisting of a filler, a binder, a disintegrant, a buffer, a preservative, an antioxidant, a lubricant, a flavoring agent, a thickener, a coloring agent, an emulsifier, a suspending agent, a stabilizer, and an isotonic agent.

The composition may include the compound of Formula 1, or a pharmaceutically acceptable salt or solvate thereof, at a "therapeutically effective dose". In the composition, the term "therapeutically effective dose" as used herein denotes a sufficient dose that produces a therapeutic effect when administered to a subject in need of treatment. The term "treatment" as used herein denotes treatment of a disease or medical condition, for example, a disease associated with demyelination, of a subject such as a mammal, including humans, and the meaning of treatment is the following: (a) ameliorating the disease or medical condition such as by eliminating or causing regression of the disease or medical condition of a patient; (b) suppressing the disease or medical condition such as by slowing or arresting the development of the disease or medical condition of a patient; or (c) alleviating a symptom of the disease or medical condition of a patient. The "effective dose" may be appropriately selected by one of ordinary skill in the art. For example, the "effective dose" may be in a range of about 0.01 mg to about 10,000 mg, 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg.

The composition may be prepared for oral administration or parenteral administration including intravenous, intraperitoneal, subcutaneous, rectal, and topical administration. Thus, the composition may be formulated into various forms such as tablets, capsules, aqueous solutions, or suspensions. In the case of tablets for oral administration, an excipient such as lactose or corn starch and a lubricant such as magnesium stearate may be added thereto in general. In the case of capsules for oral administration, lactose and/or dried corn starch may be used as a diluent. When an aqueous suspending agent for oral administration is needed, active ingredients may be attached to an emulsifier and/or a suspending agent. If necessary, a predetermined sweetening agent and/or a flavoring agent may be added to the composition. In the case of intraneural, intramuscular, intraperitoneal, subcutaneous, and intravenous administration, a sterilized solution of the active ingredients is generally prepared, and the pH of the solution needs to be appropriately adjusted and buffered. In the case of intravenous administration, the total concentration of solutes needs to be controlled to render the preparation isotonic. The composition may be formulated in the form of an aqueous solution including a pharmaceutically acceptable carrier such as salt water at a pH of 7.4. The solution may be administered to intramuscular or intraneural blood flow of a patient by local bolus injection.

The compound of Formula 1 or a pharmaceutically acceptable salt or solvate thereof may have effects of suppressing demyelination or recovering demyelinated neurons by remyelinating neurons.

The composition may be used in combination with at least one other treatment agent for treating a disease associated with demyelination. Alternatively, the composition may be used without active ingredients for treating a disease associated with demyelination other than the compound of Formula 1 or a pharmaceutically acceptable salt or solvate of the compound of Formula 1.

According to another aspect of an exemplary embodiment, provided is a use of the compound of Formula 1 defined above, or a pharmaceutically acceptable salt or solvate thereof, for treating a disease associated with demyelination.

According to another aspect of an exemplary embodiment, provided is a use of the compound of Formula 1 defined above or a pharmaceutically acceptable salt or solvate thereof for preparing a medication for treating a disease associated with demyelination.

According to another aspect of an exemplary embodiment, provided is a method of accelerating remyelination or suppressing demyelination of neurons in a mammal, the method including administering a compound of Formula 1 or a pharmaceutically acceptable salt or solvate thereof to the mammal at an effective dose to accelerate remyelination:

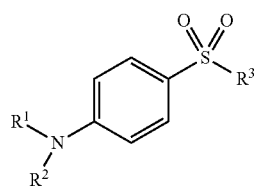

(Formula 1)

In Formula 1, $R^1$ and $R^2$ are each independently H or —(C=O)(C1-C6 alkyl), or $R^1$ and $R^2$ together constitute =N-phenyl, in which the phenyl is substituted with a carboxyl group and a hydroxyl group; and $R^3$ is an aminophenyl, in which an H of the amino group is optionally substituted with —(C=O)(C1-C6 alkyl), or $R^3$ is —$NR^6R^7$, in which —$R^6$ and $R^7$ are each independently H, —(C=O) (C1-C6 alkyl), or a heteroaryl having 3 to 8-membered ring atoms. All aspects of the method, including the compound of Formula 1 used in accordance with the method, and specific embodiments, are as previously described with respect to the pharmaceutical composition.

The compound of Formula 1 or salt or solvate thereof may be administered to a subject. When the "effective dose to accelerate remyelination" is administered to the subject in need of remyelination, the term denotes a sufficient dose that produces a remyelination effect.

According to another aspect of an exemplary embodiment, provided is a method of treating a disease associated with demyelination of neurons in a mammal, the method including accelerating remyelination of neurons by administering a compound of Formula 1 or a pharmaceutically acceptable salt or solvate thereof to the mammal with a disease associated with demyelination of neurons at a therapeutically effective dose:

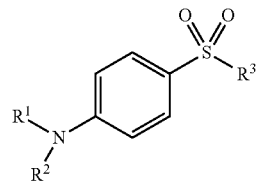

(Formula 1)

In Formula 1, $R^1$ and $R^2$ are each independently H or —(C=O)(C1-C6 alkyl), or $R^1$ and $R^2$ together constitute =N-phenyl, in which the phenyl is substituted with a carboxyl group and a hydroxyl group; and $R^3$ is an aminophenyl, in which an H of the amino group is optionally substituted with —(C=O)(C1-C6 alkyl), or $R^3$ is —$NR^6R^7$, in which —$R^6$ and $R^7$ are each independently H, —(C=O) (C1-C6 alkyl), or a heteroaryl having 3- to 8-membered cyclic atoms. All aspects of the method, including the compound of Formula 1 used in accordance with the method, and specific embodiments, are as previously described with respect to the pharmaceutical composition.

Regarding the method, the terms "a compound of Formula 1 or a pharmaceutically acceptable salt or solvate thereof", "a therapeutically effective dose", and "a disease associated with demyelination" as used herein are the same as described above. The administration may refer to administration of the composition including the "compound of Formula 1 or a pharmaceutically acceptable salt or solvate thereof".

Regarding the method, one of ordinary skill in the art may appropriately select a route of the administration. The route of the administration may be oral, parenteral, or local administration.

An administration dose may vary depending on the condition of a patient, an administration route, and a doctor's decision. An effective administration dose may be inferred by a dose-response curve derived from an in vitro or animal model test system. A ratio and a concentration of the compound of an embodiment in the composition to be administered may be determined according to chemical characteristics, an administration route, and a therapeutic administration dose. The dose may be administered to a subject, for example, at an effective dose of about 1 µg/kg to about 1 g/kg per day, or about 0.1 mg/kg to about 500 mg/kg per day. The dose may be changed depending on an age, sensitiveness, or symptoms of the subject.

The present invention will be described in further detail with reference to the following examples. These examples are for illustrative purposes only and are not intended to limit the scope of the present invention.

Example 1

(1) Effect of DDS, MADDS, SSZ, and SCM on PMP22 Expression In Vitro

SH-SY5Y cells were inoculated at a concentration of $10^5$ cells/ml in each well of a 12-well plate including 2 ml of a DMEM medium containing 10% FBS, 100 units/ml of penicillin, and 100 units/ml of streptomycin and incubated until the cell density was about 60% to about 65% in a 5% $CO_2$ incubator at 37°. Then, dapsone (4,4'-diaminodiphenylsulfone, DDS) (available from Sigma), MADDS (available from Sigma), SSZ (available from Sigma), and SCM (available from Sigma) were respectively added to the wells at various concentrations and incubated for 24 hours under the same conditions. Vitamin C (ascorbic acid, AA) (available from Sigma) was used as the positive control group. Vitamin C is known as having an effect of treating peripheral neuropathy by using a cAMP modulator. SH-SY5Y cells are a human-derived cell line used in scientific research. The original cell line, SK-N-SH from which SH-SY5Y cells were subcloned, was isolated from a bone marrow biopsy taken from a four year-old female with neuroblastoma. SH-SY5Y cells are often used as in vitro models of neuronal function and differentiation. The SH-SY5Y cells used herein have been modified to consistently overexpress the human PMP22 gene by lentiviral mediated integration of PMP22 into a chromosome.

After removing 2 ml of the culture medium, the SH-SY5Y cells were washed with phosphate buffered saline (PBS), and a lysis solution, 0.5% Triton X-100, in PBS was added thereto. Then, cells were collected using a scraper, left in ice for 30 minutes, and then, the cells were disrupted. Using a bicinchoninic acid (BCA) protein assay, the amount of protein in each sample was normalized to 1 ug/ul. SDS-PAGE (Invitrogen) was performed on the sample, and then Western blotting was performed with rabbit anti-PMP22 (Novus biological) and rabbit anti-actin (Sigma) primary antibodies, and an anti-rabbit secondary antibody.

Figure 1B:
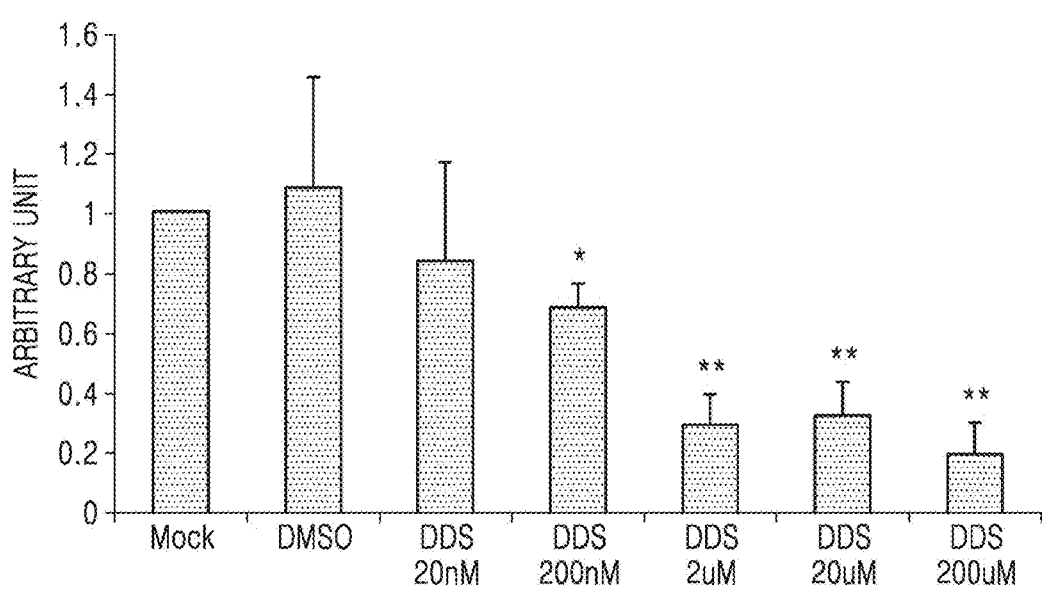

FIGS. 1A and 1B illustrate the results of α-PMP22 gene expression analysis of SH-SY5Y cells in the presence of DDS measured by Western blotting. FIG. 1A is an image of the Western blot, and FIG. 1B illustrates the results in a graph of intensities or densities of each band of the Western blot measured by using an Image J program. In FIGS. 1A and 1B, "Mock" represents a non-treatment group, "DMSO" represents a control group which is treated with the solvent DMSO instead of DDS, and "DDS" represents a test performed with DDS added to DMSO at predetermined concentrations. The test was performed by a multiple of 4 (n=4), * denotes a statistical significance p value of 0.05 or less, and ** denotes a statistical significance p value of 0.01 or less. As shown in FIGS. 1A and 1B, as the concentration of DDS increases, the amount of PMP22 protein decreased.

Also, RNA from treated and untreated SH-SY5Y cells was extracted by with Trizol (Invitrogen). PM22 gene expression was analyzed by using a one-step RT-PCR kit (Qiagen), whereby the extracted RNA was mixed with a PMP22 gene specific primer set of SEQ ID NOS: 1 and 2, and a real time-PCR (RT-PCR) was performed to confirm the degree of mRNA expression.

Figure 2:
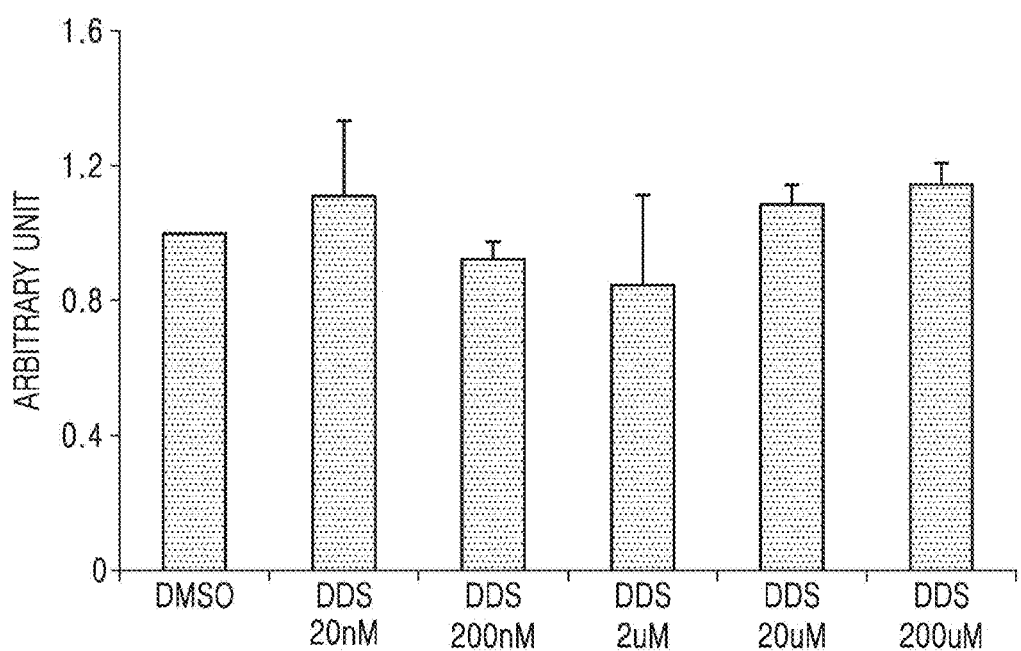
FIG. 2 illustrates α-PMP22 gene expression of SH-SY5Y cells in the presence of DDS measured by RT-PCR at the mRNA level.

FIG. 2 illustrates the results of α-PMP22 gene expression of SH-SY5Y cells in the presence of DDS measured by RT-PCR at the cDNA level. As shown in FIG. 2, expression of PM22 mRNA did not show a significant difference according to a DDS concentration.

By referring to FIGS. 1A, 1B, and 2, it may be known that DDS controls and reduces expression of PMP22 by regulation at a protein level. Thus, DDS is deemed as being involved in a decomposition pathway of PMP22 and promoting PMP22 decomposition, but the scope of embodiments is not limited to a specific mechanism.

Figure 3A:
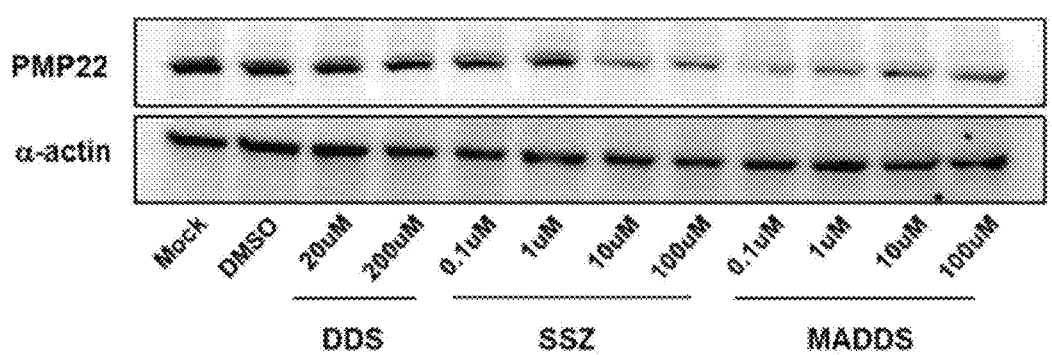
FIGS. 3A and 3B illustrate α-PMP22 gene expression of SH-SY5Y cells in the presence of DDS, SSZ, and MADDS measured by Western blot.
Figure 3B:
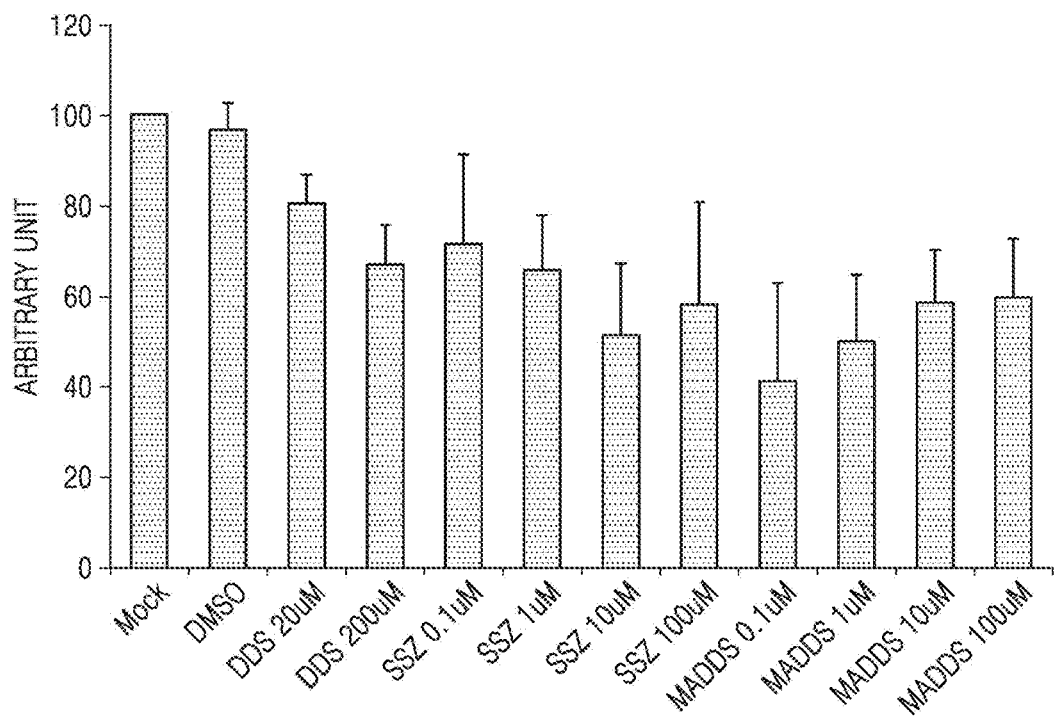

FIGS. 3A and 3B illustrate the results of α-PMP22 gene expression of SH-SY5Y cells in the presence of DDS, SSZ, and MADDS measured by Western blot. FIG. 3A is an image of the Western blot, and FIG. 3B illustrates the results in a graph of intensities or densities of each band of the Western blot image measured with the Image J program. In FIGS. 3A and 3B, "Mock" represents a non-treatment group, "DMSO" represents a control group which is treated with the solvent DMSO, instead of DDS, and "DDS", "SSZ", and "MADDS" represent a test performed with DDS, SSZ, and MADDS that are each added to DMSO at a respective predetermined concentration. The test was performed by a multiple of 2 (n=2). As shown in FIGS. 3A and 3B, when DDS, SSZ, and MADDS were each added, the amount of the PMP22 protein decreased about 20% to about 60%, compared to that of the control group.

Figure 4A:
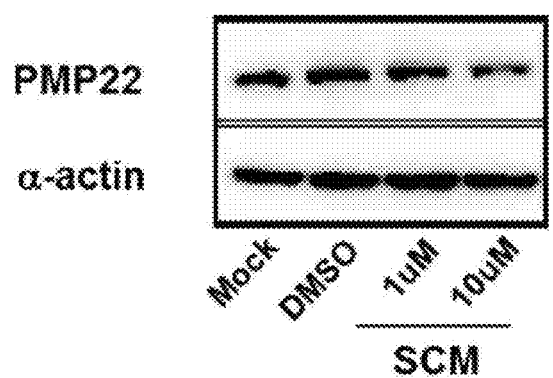
FIGS. 4A and 4B illustrate α-PMP22 gene expression of SH-SY5Y cells in the presence of SCM measured by Western blot.
Figure 4B:
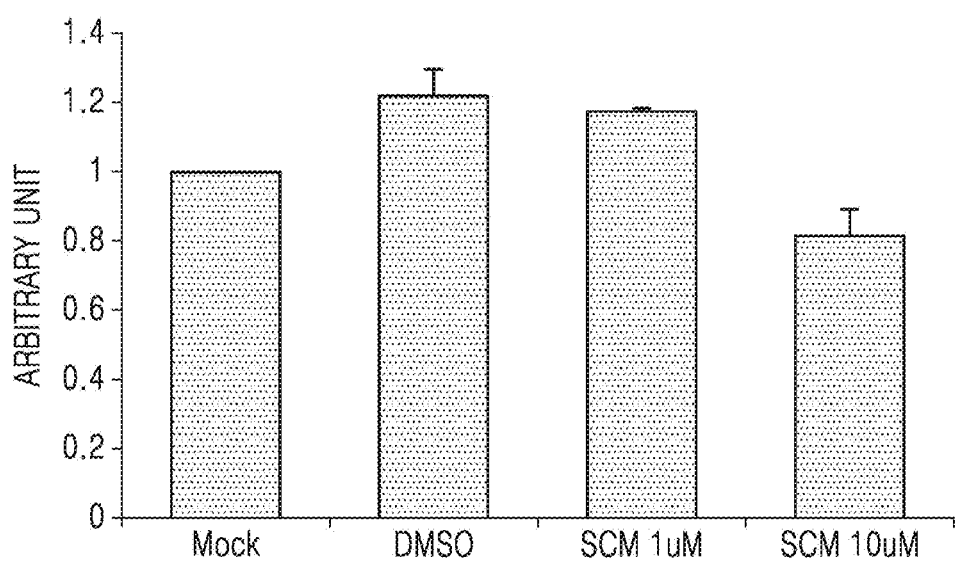

FIGS. 4A and 4B illustrate the results of α-PMP22 gene expression of SH-SY5Y cell strains in the presence of SCM measured by Western blot. FIG. 4A is an image of the Western blot, and FIG. 4B illustrates the results in a graph of intensities or densities of each band of the Western blot image measured by using the Image J program. In FIGS. 4A and 4B, "Mock" represents a non-treatment group, "DMSO" represents a control group which is treated with the solvent DMSO, instead of SCM, and "SCM" represents a test performed with SCM added to DMSO at a predetermined concentration. As shown in FIGS. 4A and 4B, when SCM was added, the amount of the PMP22 protein decreased compared to that of the control group.

Figure 5A:
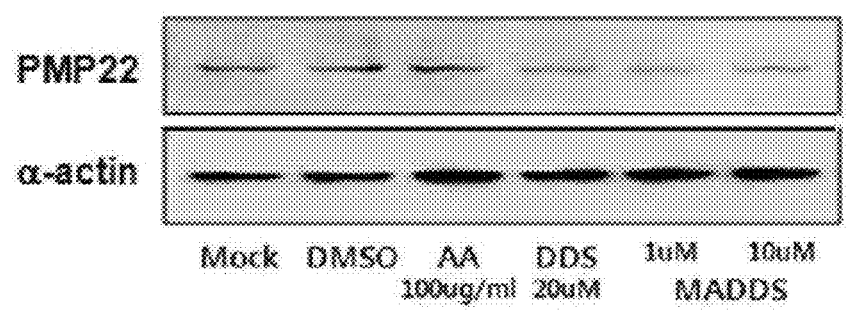
FIGS. 5A and 5B illustrate α-PMP22 gene expression of SH-SY5Y cells in the presence of AA, DDS, and MADDS measured by Western blot.
Figure 5B:
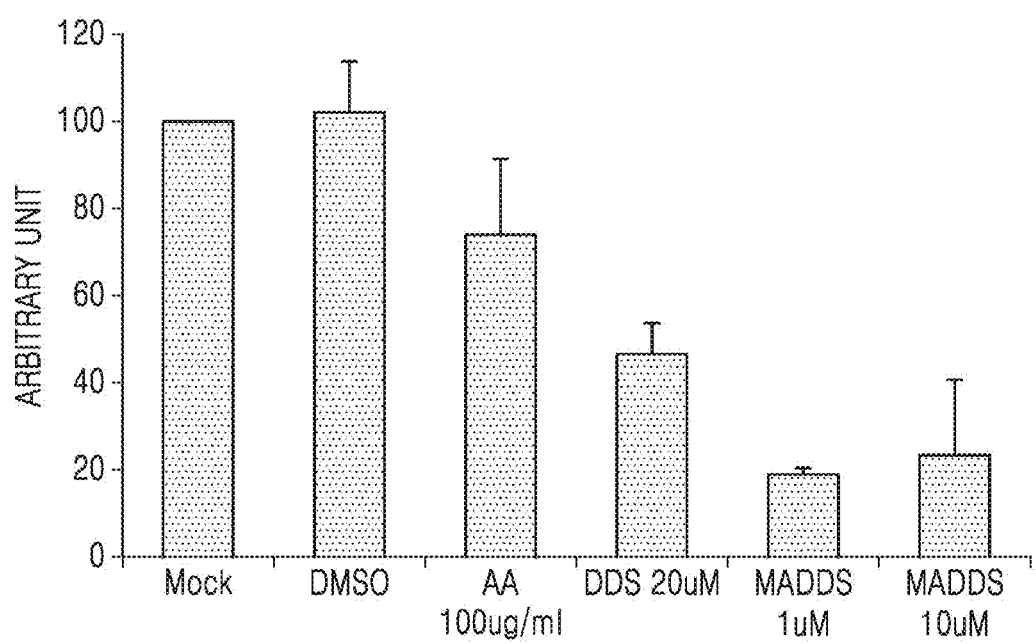

FIG. 5A and FIG. 5B illustrate the results of α-PMP22 gene expression of SH-SY5Y cells in the presence of AA, DDS, and MASS measured by Western blot. FIG. 5A is an image of the Western blot, and FIG. 5B illustrates the results in a graph of intensities or densities of each band of the Western blot image measured by using the Image J program. In FIGS. 5A and 5B, "Mock" represents a non-treatment group, "DMSO" represents a control group which is treated with the solvent DMSO, instead of AA, DDS, or MADDS, and "AA", "DDS", and "MADDS" represent a test performed with AA, DDS, and MADDS that are each added to DMSO at a respective predetermined concentration. As shown in FIGS. 5A and 5B, when DDS and MADDS were each added, the amount of the PMP22 protein significantly decreased compared to those of a negative control group and a positive control group, in which AA was added.

(2) Effect of DDS, MADDS, SSZ, and SCM on PMP22 Expression In Vivo

Zebrafish (*Danio rerio*), in which a gene encoding an Mbp:EGFP fusion protein that is specifically expressed in myelin and emits fluorescence by using a promoter of a myelin basic protein (MBP) gene, was prepared. These Mbp:EGFP expressing zebrafish where then further modified to model demyelinating diseases. Specifically, the NfsB toxic gene encodes a nitroreductase (NTR) enzyme. In general, NTR does not have any cytotoxicity in typical zebrafish, but when metronidazole (Mtz) is administered, a cell converts Mtz into a cytotoxic material, and apoptosis may be induced due to the cytotoxic material. Genetically engineered zebrafish were prepared that express the NfsB toxic gene specifically in a differentiated oligodendrocyte and Schwann cell by using the promoter of an MBP gene (specifically expressed in myelin) and the Gal4-UAS transactivator system. Next, it was confirmed that the NfsB toxic gene was myelin-specifically expressed in the genetically engineered zebrafish.

Then, when the Mtz matrix was added to the genetically engineered zebrafish, apoptosis was induced oligodendrocyte-specifically in the, and thus, generation of demyelination was confirmed. As a result, in the presence of Mtz, an animal model of demyelination generation was established.

The added Mtz matrix was removed from the culture medium, and the genetically engineered zebrafish were cultured in culture medium free of Mtz for 1 week followed by a recovery period. This study confirmed that remyelination of the demyelinated central nervous system and peripheral nervous system occurred naturally, and an effect of DDS, MADDS, SSZ, and SCM drugs on the promotion of remyelination was confirmed.

In particular, 100 zebrafish were incubated in egg water or an embryo medium (EM) (which includes 15 mM NaCl, 0.5 mM KCl, 1 mM $CaCl_2$, 1 mM $MgSO_4$, 0.15 mM $KH_2PO_4$, 0.05 mM $NH_2PO_4$, and 0.7 mM $NaHCO_3$) at 28.5° in 1 L of water in a water tank for 4.5 dpf (days post-fertilization) from birth date, and then, 10 mM of MTZ (Sigma) dissolved in an EM including 0.2% DMSO was added thereto for 36 hours of demyelination. Each of the zebrafish was transferred to a well with each of the drugs in a 96-well plate and was incubated at 28.5°. Some of the zebrafish were remyelinated by removing Mtz in the EM by washing the zebrafish with a new EM three times after 6 dpf. 10 uM of DDS, MADDS, SSZ, and SCM were each added to the remaining zebrafish and incubated under the same conditions. A control group was incubated under the same condition except that 0.2% DMSO was added instead of adding MTZ.

Figure 6:
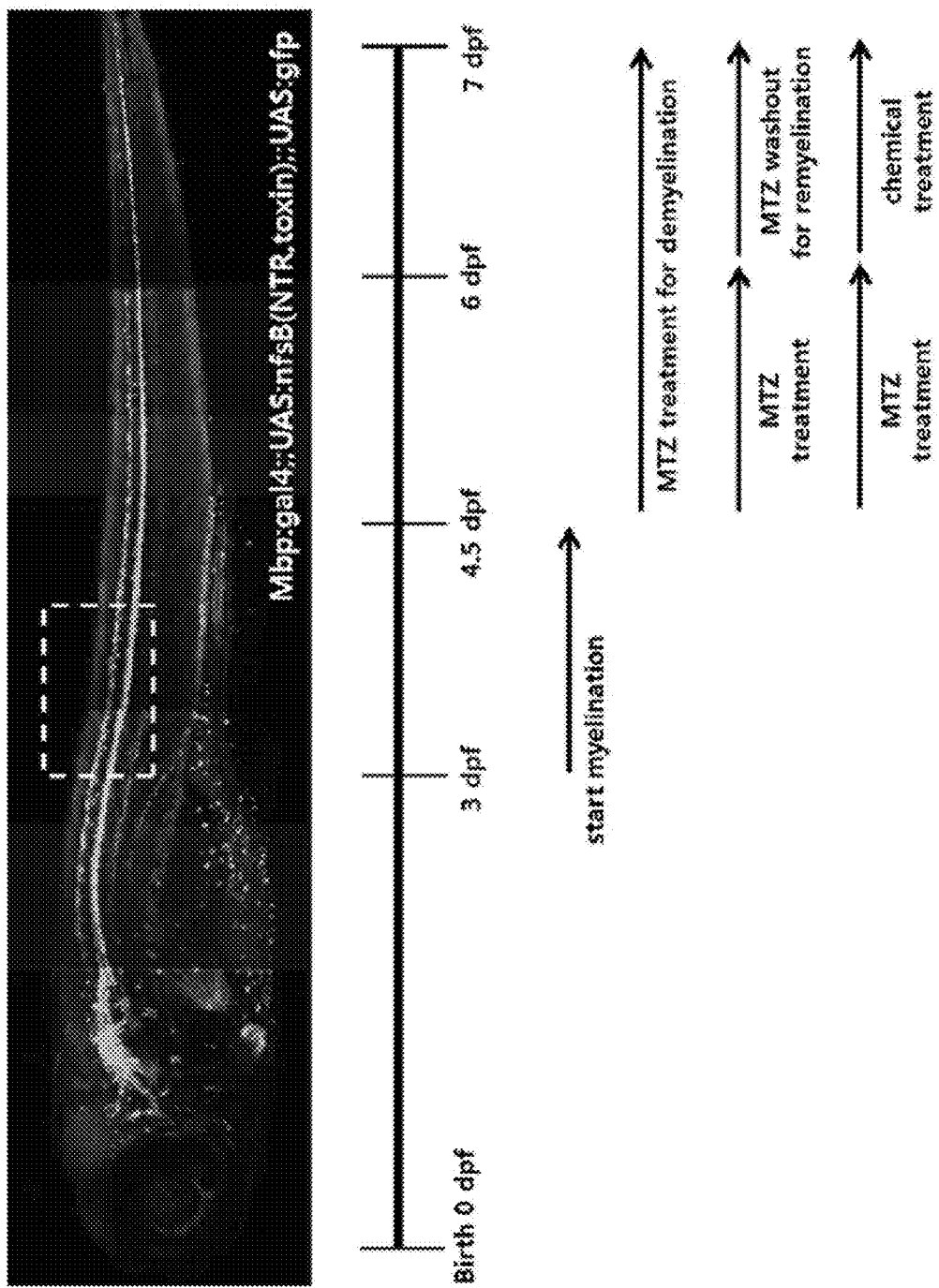
FIG. 6 is an image of a zebrafish (Mbp:gal4;USA:nfsB (NTR, toxin);UAS:gfp) taken with a confocal laser microscope.

FIG. 6 is an image of a zebrafish (Mbp:gal4;USA:nfsB (NTR, toxin);UAS:gfp), taken by a confocal laser microscope (Olympus). In FIG. 6, a white dashed line box is a part to be monitored for remyelination in myelin of the central nervous system and the peripheral nervous system. A lower part of FIG. 6 illustrates a process of the test, where myelination was generated in the zebrafish after 3 dpf from the birth date, MTZ was treated at 4.5 dpf, MTZ was washed or removed at 6 dpf (hereinafter, referred to as "recovery 1 day"), and 10 uM of each of DDS, MADDS, SSZ, and SCM was added thereto. The test was performed until 7 dpf. The test was performed by a multiple of 18 (n=18).

Figure 7:
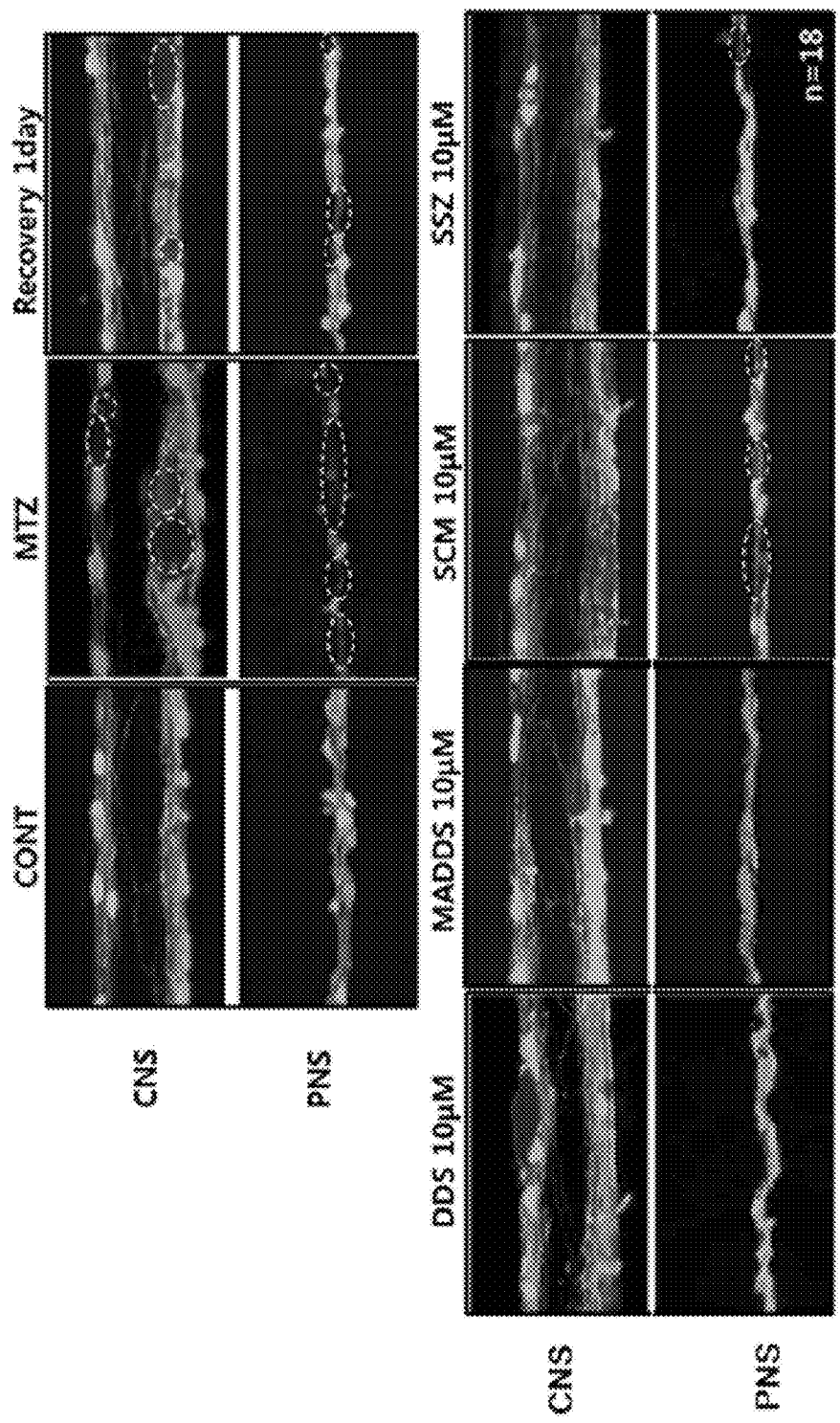
FIG. 7 shows confocal laser microscope images of the central nervous system and peripheral nervous system of zebrafish treated with MTZ, DDS, MADDS, SSZ, or SCM, where the white dashed line shows a region where fluorescence disappeared due to demyelination.

FIG. 7 shows images of the central nervous system and peripheral nervous system of zebrafish that are each respectively treated with MZT, DDS, MADDS, SSZ, and SCM, where the images are taken by a confocal laser microscope (Olympus). In FIG. 7, "CNS" denotes the central nervous system, and "PNS" denotes the peripheral nervous system. The "CNS" and "PNS" were the measured myelin sites in the white dashed line region. In FIG. 7, the white dashed line shows a region where fluorescence disappeared due to demyelination and where change in myelination occurred, compared to that of the control group. In FIG. 7, a fluorescent intensity is proportional to a degree of myelination.

Figure 8A:
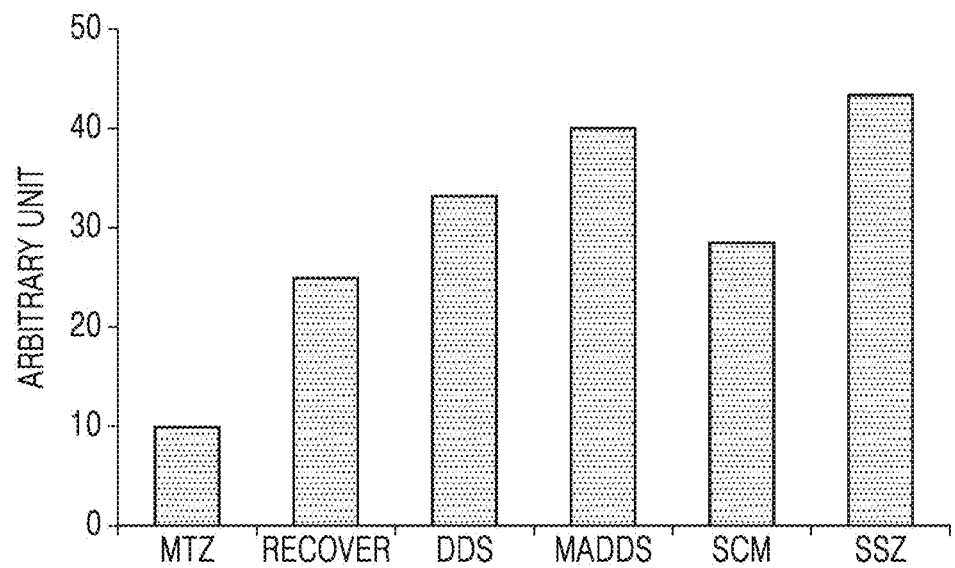
FIGS. 8A and 8B illustrate the results of fluorescent intensity with respect to the same area of the CNS (FIG. 8A) and PNS (FIG. 8B) shown in FIG. 7.
Figure 8B:
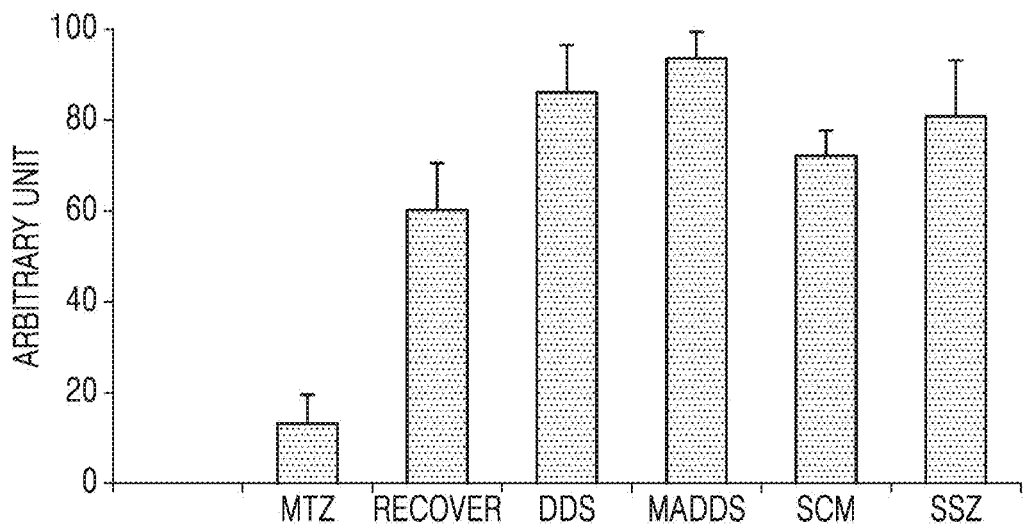

FIGS. 8A and 8B illustrate the results of fluorescent intensity with respect to the same area of myelination site of CNS and PNS. As shown in FIGS. 8A and 8B, myelination at CNS (FIG. 8A) and PNS (FIG. 8B) significantly increased, compared to that in the control group.

Example 2

Effect of Sulfasalzine on an In Vivo Mouse Model of CMT

In this example, the effect of sulfasalzine on the CMT was investigated using Trembler-J (Tr-J) mice. The Tr-J mouse has a missense mutation in the murine peripheral myelin protein-22 gene (Pmp22). Pmp22 mutations are believed to cause the neuropathies of Charcot-Marie-tooth disease in humans (*Nature* 356, 241-244 (19 Mar. 1992); doi:10.1038/356241a0). Two month old heterozygous $Tr^J$ mice in the C57BL/6J background were obtained from Jackson Laboratories (Bar Harbor, Me.). Matings between Tr-J heterozygous females and males in the C57BL/6 genetic background were implemented to generate Tr-J heterozygous and wild-type controls.

(1) Materials and Methods

Animals

Male and female C57BL/6J background mice were obtained from Jackson Laboratories (Bar Harbor, Me.) and maintained at 12-hr dark/light cycles in air controlled rooms, with free access to food and water. All efforts were made to minimize animal suffering from pain and discomfort and to reduce the number of animals used. After 1 week adaptation to laboratory conditions, the animals were randomly assigned to experimental groups consisting of 4-5 mice.

All experiments involving animals were approved and confirmed by the Sungkyunkwan University Ethical Committee in accordance with international guidelines.

Drugs

Sulfasalazine was obtained from Sigma-Aldrich, St. Louis. Sulfasalazine (50 mg/kg daily) was administered orally to female mice (n=4-5 per group) via sulfasalazine-containing drinking water. Before sulfasalazine oral intervention, weight and daily water intake of the mice was measured to determine the dose of sulfasalazine. Each Tr-J and WT mice were administered sulfasalazine drinking water for 2 months (50 mg/kg daily).

(2) Behavior Assessment by Rotarod Test

Each mouse was placed on a rotating rod (30 mm in diameter) spinning at 4 rpm after 2 months treatment. The mice were first placed on the rubber-covered rod and left for 30 sec on the rod without rotation. Once stabilized, mice were subjected to an incrementally increasing speed of 1 rpm per 8 s. Each animal underwent three trials. The average length of time that the mice managed to remain on the rod was recorded. (2) Morphological study by toluidine blue (TB) staining and g-ratio After 2 months oral intervention, sciatic nerves were harvested from mice (WT+/−50 mg/kg sulfasalazine and Trembler J+/−50 mg/kg sulfasalazine). Nerves were fixed in 2% (w/v) glutaraldehyde in 0.1 M phosphate buffer (pH 7.4) for 4 h, followed by washing with 0.1 M phosphate buffer. After immersion in 8% (w/v) sucrose solution, samples were embedded in Eponate (Ted Pella, Calif.). Each section was stained with toluidine blue. Sample sections were evaluated using light microscopy.

(3) Muscle Function by Measurement of Twitch/Tetanus Isometric Force

In order to examine whether sulfasalazine has an effect on twitching and tetanizing when electric stimulation is applied to muscle, the isometric force of muscle was measured. Specifically, in order to separate muscle from 2-month treated mice (Trembler J+/−50 mg/kg sulfasalazine), the mice were anesthetized by injection with sodium pentobarbital (100 mg/kg body weight). One soleus (SOL) tendon was carefully separated from the hindlimb of each mouse, and the muscle tissues were set and stabilized in oxygen-treated Ringer's solution (25° C., 118 mM NaCl, 4.75 mM KCl, 2.5 mM $CaCl_2$, 1.18 mM $MgSO_4$, 1.18 mM $NaH_2PO4$, 24.8 mM $NaHCO_3$, 10 mM glucose, 0.02 g/L tubocurarine chloride, pH 7.4). One end of the tendon was anchored to a tissue bath, which was filled with Ringer's solution, and to which oxygen was smoothly supplied, and the other end was anchored to a isometric force transducer (Model FT03 Grass instruments, West Warwick, R.I.). The twitch and tetanus of the muscle were adjusted by the intensity of electric stimulation. The muscle was stabilized in Ringer's solution for 10 minutes, and then an experiment for muscle contraction function was carried out.

(4) Results

Figure 9:
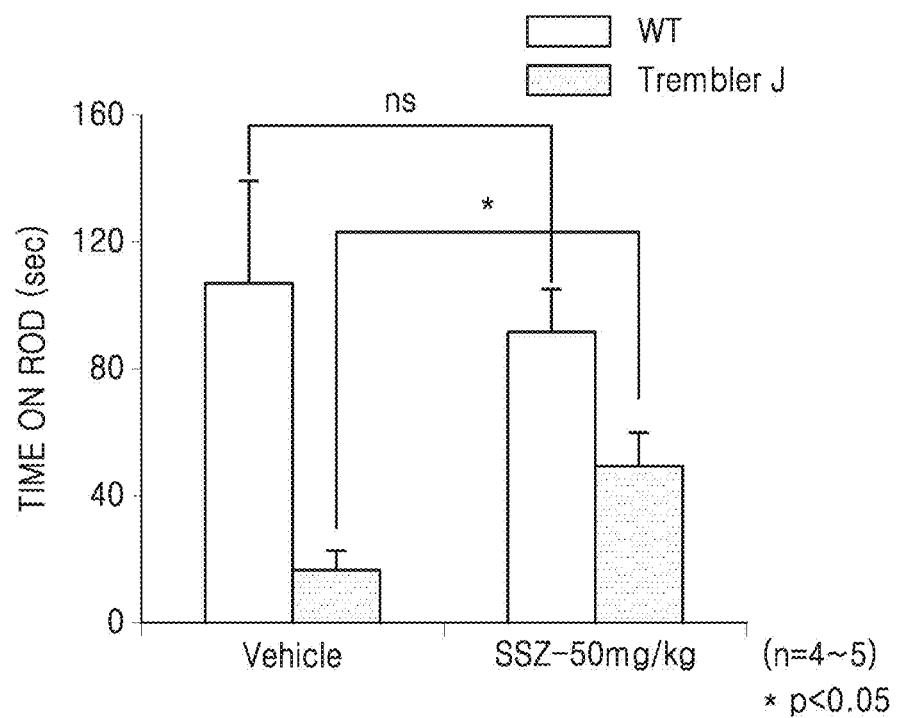
FIG. 9 illustrates Rotarod test results for sulfasalazine-treated and placebo-treated Tr-J mice (CMT mouse model)

FIG. 9 illustrates the Rotarod test results for sulfasalazine-treated and placebo-treated Tr-J mice (CMT mouse model). In the FIG. 9, SSZ-50 mg/kg represents the results for Tr-J SSZ treated mice (50 mg/kg SSZ per day for 2 months), vehicle represents the results from placebo-treated Tr-J mice (treated daily for 2 months). According to the FIG. 9, the time on rod was significantly increased for the SSZ-treated Tr-J mice compared to the placebo-treated Tr-J mice, while the time on rod was decreased for the SSZ-treated WT mice compared to the placebo-treated WT mice. This indicates that SSZ improves the locomotor capacity of the Tr-J mice (CMT mouse model).

Figure 10A:
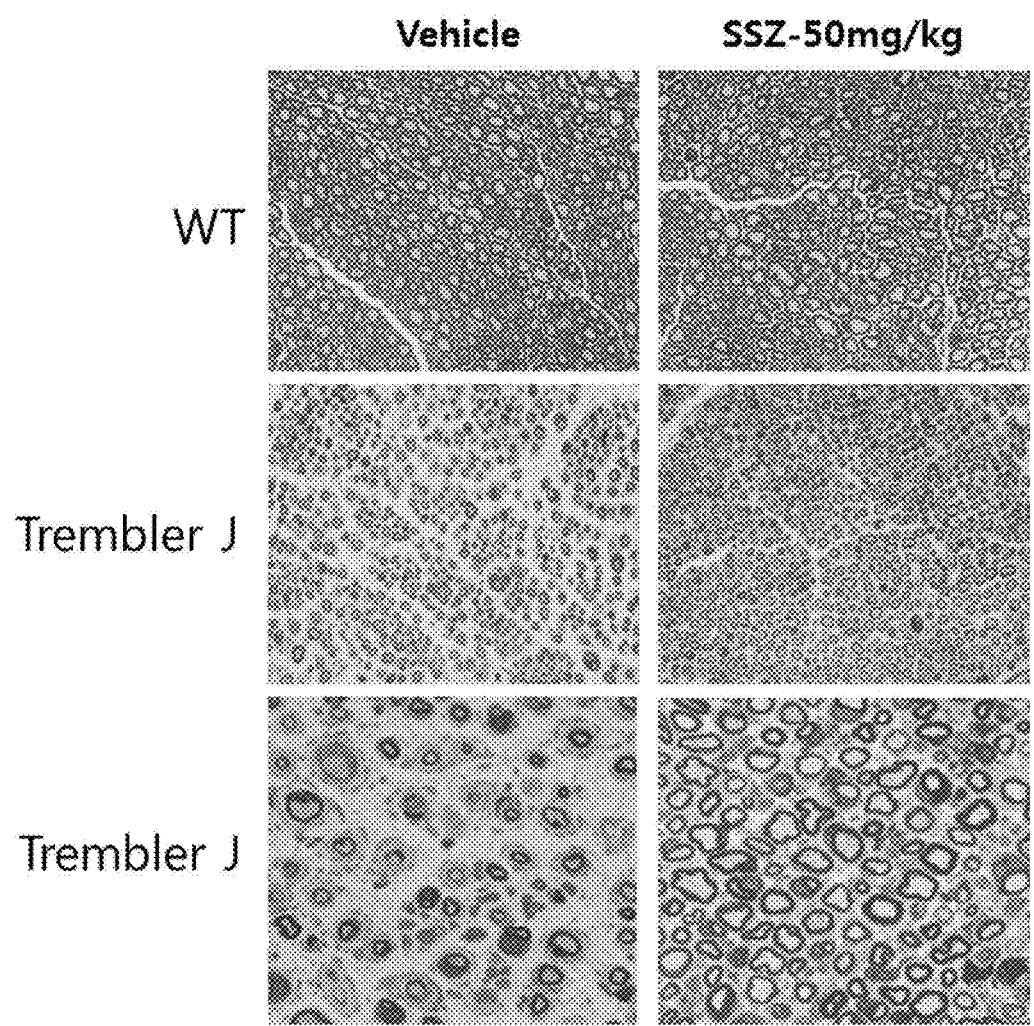
FIGS. 10A-C show the (A) microscopic image, (B) g-ratio definition, and (C) calculated g-ratio of the sciatic nerve of a sulfasalazine-treated Tr-J mouse.
Figure 10B:
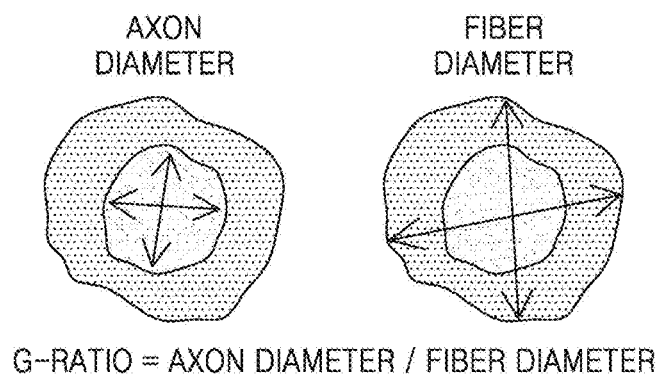
Figure 10C:
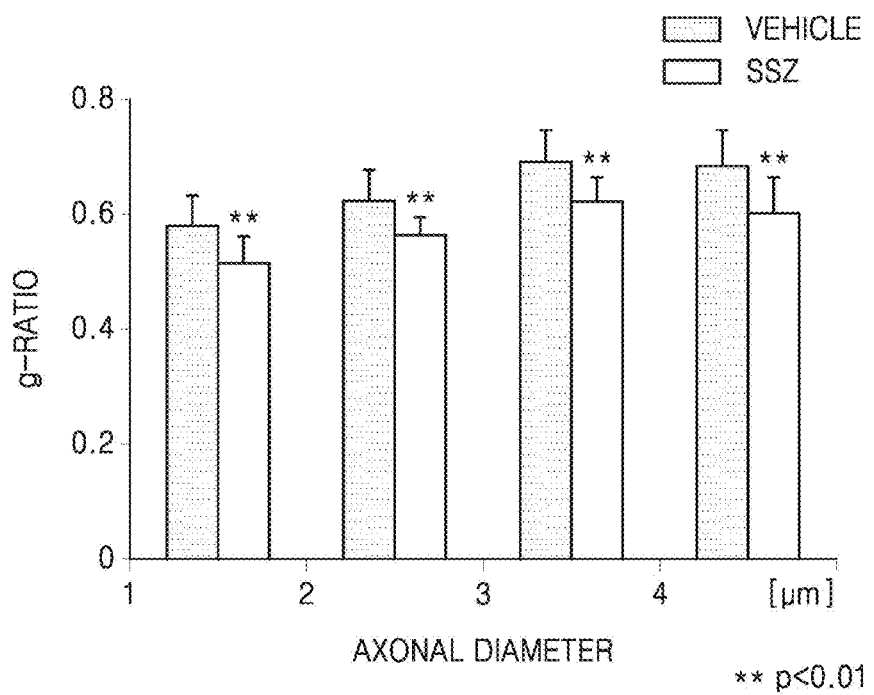

FIGS. 10A-C represent the microscopic image(A), definition of g-ratio(B), and g-ratio(C) of the sciatic nerve of a sulfasalazine-treated Tr-J mouse. As shown in FIG. 10A, the mouse sciatic nerve was stained with toluidine blue, which stains the myelin of sciatic nerve blue. FIG. 10A indicates that number of myelinated axons in the sulfasalazine-treated Tr-J mouse sciatic nerve was significantly increased compared to the vehicle-treated Tr-J mouse. FIG. 10C represents the average g-ratio (illustrated in FIG. 10B) for each axonal diameter for <2 um, 2 to 3 um, 3 to 4 um, and >4 um axonal diameter. As shown in FIG. 10C, the g-ratio of SSZ treated Tr-J mice was significantly lower than vehicle treated Tr-J mice. This indicates a significant increase in myelination in the sciatic nerve of SSZ-treated Tr-J mice as compared to vehicle treated Tr-J mice.

Figure 11A:
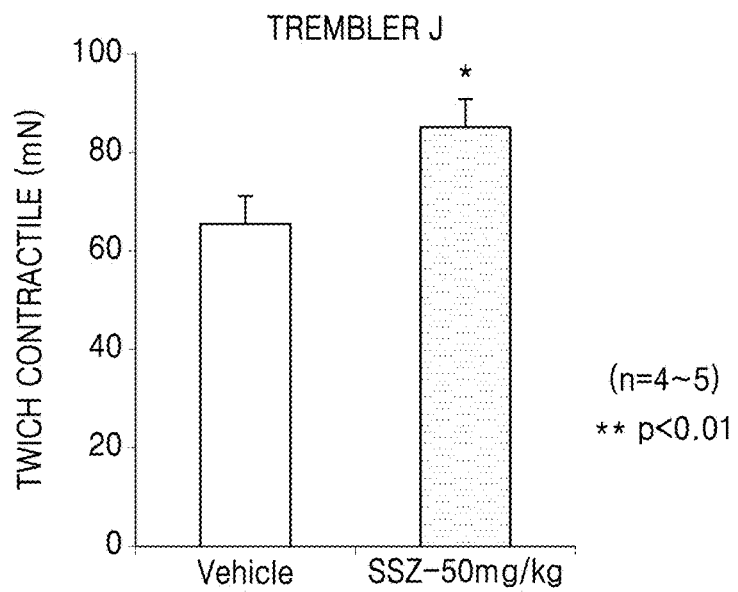
FIGS. 11A and 11B illustrate the results from twitch and tetanus contraction experiments in the Soleus tendon of SSZ treated Tr-J mouse.
Figure 11B:
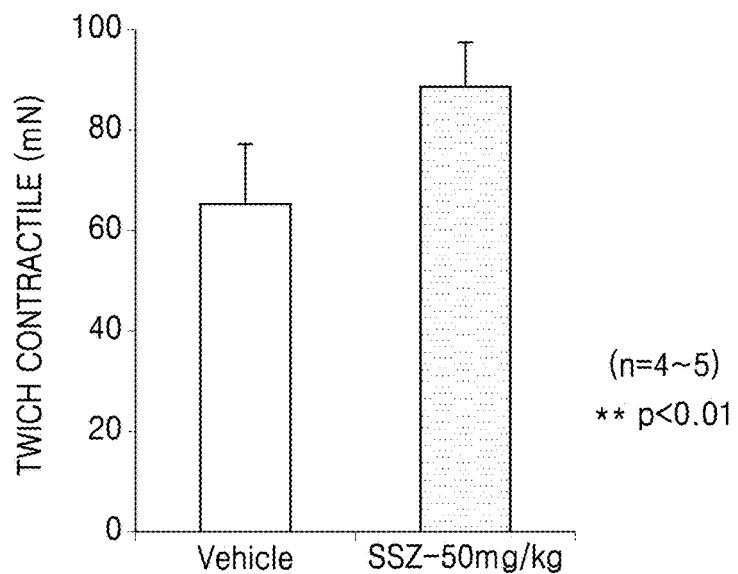

FIGS. 11A and 11B represent twitch and tetanus contraction in Soleus tendon of SSZ treated Tr-J mouse. As shown in FIGS. 11A and 11B, twitch and tetanus contraction were significantly increased in SSZ treated Tr-J mice compared to respective placebo-treated mice. This indicates that SSZ improves the muscle function of the Tr-J mice.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating Charcot Marie Tooth (CMT) disease, the method comprising administering sulfasalazine, without another active ingredient, at a therapeutically effective dose to a mammal having CMT disease.

2. The method of claim 1, wherein the CMT is a CMT1A subtype, a CMT1E subtype, or a CMT3 subtype.

3. The method of claim 1, wherein the mammal is a human.

* * * * *